(12) United States Patent
Link

(10) Patent No.: US 7,628,813 B2
(45) Date of Patent: Dec. 8, 2009

(54) CERVICAL INTERVERTEBRAL PROSTHESIS SYSTEM

(75) Inventor: Helmut D. Link, Hamburg (DE)

(73) Assignee: Cervitech, Inc., Rockaway, NJ (US)

( * ) Notice: Subject to any disclaimer, the term of this patent is extended or adjusted under 35 U.S.C. 154(b) by 0 days.

(21) Appl. No.: 10/687,933

(22) Filed: Oct. 20, 2003

(65) Prior Publication Data

US 2005/0085911 A1    Apr. 21, 2005

(51) Int. Cl.
*A61F 2/44* (2006.01)
(52) U.S. Cl. .................................................. 623/17.11
(58) Field of Classification Search ............. 623/17.11, 623/17.14, 17.15, 17.16, 18.11, 23.47, 23.58; 606/60, 61, 63, 90, 105
See application file for complete search history.

(56) References Cited

U.S. PATENT DOCUMENTS

| | | | |
|---|---|---|---|
| 1,174,757 A | 3/1916 | Packer | |
| 3,154,072 A | 10/1964 | Mack | |
| 4,384,372 A | 5/1983 | Rector | |
| 4,627,109 A | 12/1986 | Carabelli et al. | |
| 4,759,766 A * | 7/1988 | Buettner-Janz et al. | .. 623/17.15 |
| 4,782,535 A | 11/1988 | Yewer, Jr. et al. | |
| 4,968,027 A | 11/1990 | Anderson | |
| 5,036,864 A | 8/1991 | Yewer, Jr. | |
| 5,046,488 A | 9/1991 | Schliek, Sr. | |
| 5,086,758 A | 2/1992 | Schiek, Sr. et al. | |
| 5,172,454 A | 12/1992 | Martignago | |
| 5,178,163 A | 1/1993 | Yewer, Jr. | |
| 5,269,050 A | 12/1993 | Yewer, Jr. | |
| 5,306,309 A * | 4/1994 | Wagner et al. | ........... 623/17.16 |
| 5,316,022 A | 5/1994 | Schiek, Sr. | |
| 5,388,274 A | 2/1995 | Glover et al. | |
| 5,401,269 A | 3/1995 | Büttner-Janz et al. | |
| 5,416,952 A | 5/1995 | Dodge | |
| 5,425,773 A | 6/1995 | Boyd et al. | |
| 5,432,951 A | 7/1995 | Yewer, Jr. | |
| 5,445,601 A | 8/1995 | Harlow | |
| 5,470,000 A | 11/1995 | Munoz | |
| 5,500,959 A | 3/1996 | Yewer, Jr. | |
| 5,507,816 A * | 4/1996 | Bullivant | .................. 623/17.15 |
| 5,534,029 A * | 7/1996 | Shima | ...................... 623/17.15 |
| 5,551,085 A | 9/1996 | Leighton | |
| 5,562,738 A * | 10/1996 | Boyd et al. | ............... 623/17.15 |
| 5,581,810 A | 12/1996 | Yewer, Jr. | |
| 5,745,959 A | 5/1998 | Dodge | |
| 5,895,428 A | 4/1999 | Berry | |

(Continued)

FOREIGN PATENT DOCUMENTS

EP    0 955 021 A1    3/1998

(Continued)

OTHER PUBLICATIONS

European Search Report dated May 17, 2004.

(Continued)

*Primary Examiner*—Eduardo C Robert
*Assistant Examiner*—David Comstock
(74) *Attorney, Agent, or Firm*—Morrison & Foerster LLP

(57) ABSTRACT

A cervical intervertebral prosthesis system includes prostheses which each have a hinge with a predefined center of hinge movement. To permit better adaptation to the different hinge radii of the cervical intervertebral disks, the cervical intervertebral prostheses of the system include at least two prostheses with different hinge radii.

4 Claims, 1 Drawing Sheet

U.S. PATENT DOCUMENTS

| | | | |
|---|---|---|---|
| 6,039,763 A * | 3/2000 | Shelokov | 623/17.16 |
| 6,053,883 A | 4/2000 | Schiek, Sr. | |
| 6,179,874 B1 * | 1/2001 | Cauthen | 623/17.14 |
| 6,350,283 B1 * | 2/2002 | Michelson | 623/17.11 |
| 6,374,464 B1 | 4/2002 | Lai | |
| 6,554,297 B2 | 4/2003 | Phillips et al. | |
| 6,610,089 B1 * | 8/2003 | Liu et al. | 623/17.11 |
| 2002/0170105 A1 | 11/2002 | Koene et al. | |
| 2004/0078079 A1 * | 4/2004 | Foley | 623/17.11 |
| 2004/0153157 A1 | 8/2004 | Keller | |

FOREIGN PATENT DOCUMENTS

| | | |
|---|---|---|
| EP | 1 166 725 | 1/2002 |
| FR | 2 718 635 | 10/1995 |
| JP | 10-234755 | 9/1998 |
| WO | WO 99/11203 | 3/1999 |
| WO | WO-02/080818 | 10/2002 |

OTHER PUBLICATIONS

Penning, L., (Jun. 1968). "Functional Radiographic Examination," Chapter I of *Functional Pathology of the Cervical Spine*. Excerpta Medica Foundation, New York; Table of Contents, 1-25.

Japanese Office Action mailed on Jul. 14, 2009 directed at counterpart application No. 2006-534602; 3 pages.

* cited by examiner

CERVICAL INTERVERTEBRAL PROSTHESIS SYSTEM

FIELD AND BACKGROUND OF THE INVENTION

The invention relates to cervical intervertebral prostheses which have a predefined center of the hinge movement. In a first known type of such prostheses, the center of the hinge movement is located inside the prosthesis (U.S. Pat. No. 5,425,773; EP-A-1166725). This does not correspond to the natural conditions which the prosthesis is intended to simulate. In another type of intervertebral prosthesis (FR-A-2718635), the hinge is formed by a pair of slide surfaces, the common center of curvature of which lies outside the prosthesis, specifically under it. This approximates to the natural conditions but is still too far remote from them.

SUMMARY OF THE INVENTION

The invention is based on the awareness that the centers of the cervical intervertebral hinge movement are different from vertebra to vertebra (L. Penning: Functional Pathology of the Cervical Spine; Excerpta Medica 1968, pages 1-23). Starting out from this realization, the invention seeks to approximate the prosthetic hinge movement more closely to the natural conditions.

The invention achieves this aim by making available a set of cervical intervertebral prostheses which comprises at least two different prostheses with a different position of the center of the hinge movement. Depending on the position in question, the operating surgeon can select a suitable prosthesis from this set and thus ensure that the movement of the intervertebral joint fitted with the prosthesis is more akin to the natural conditions than was hitherto possible.

This applies especially when the intervertebral prostheses comprise a pair of slide surfaces for forming the hinge. In this case, the two different prostheses differ from one another in terms of the different radii of curvature of their slide surface pairs. According to the invention, a prosthesis intended for a pair of vertebrae lying more in the cranial direction ought to have a greater radius of curvature of its slide surfaces than does a prosthesis which is intended for a pair of vertebrae lying more in the caudal direction.

In some cases it may suffice if the prosthesis set comprises only two prostheses with a different radius of curvature of its slide surfaces, namely a prosthesis with a radius of curvature of its slide surfaces above a defined mean value and a prosthesis with a radius of curvature of its slide surfaces below a defined mean value. This mean value is expediently 18 mm. For example, a set can comprise a first prosthesis with a radius of curvature of its slide surfaces of 22 mm and another prosthesis with a radius of curvature of its slide surfaces of 14 mm. It is desirable to have a larger number of prostheses with a different slide surface radius, for example the set cited in the example just cited can be supplemented by a prosthesis with a slide surface radius of 18 mm and if appropriate a further prosthesis with a slide surface radius of 10 mm.

The invention also relates to a method for determining which intervertebral prosthesis from a plurality of intervertebral prostheses with different hinge radius is suitable for replacing a cervical intervertebral disk. This method is distinguished in that the hinge radius of the affected joint is determined and a prosthesis with a hinge radius approximating to this hinge radius is selected. In this context, the hinge radius 20 is to be understood as the distance between the center of the hinge movement and the midpoint of the prosthesis. The method can be implemented by the physician. However, because of the existing damage, the physician will in general no longer be able to determine the movement characteristics of the joint that is to be replaced. He will therefore rely on the manufacturer of the prostheses carrying out suitable tests, whose results can also subsequently be consulted in the literature, and on said manufacturer then assigning the available prostheses, which are put together in sets, to specific intervertebral spaces. The table below shows an example of how the radii of curvature of the slide surfaces are assigned to the individual intervertebral spaces within defined size ranges (in millimeters).

| Intervertebral space | "Large" series | "Medium" series | "Small" series |
|---|---|---|---|
| C2/C3 | 22 | 20 | 18 |
| C3/C4 | 22 | 18 | 18 |
| C4/C5 | 18 | 18 | 16 |
| C5/C6 | 18 | 14 | 14 |
| C6/C7 | 14 | 14 | 12 |

As regards the use of small radii of curvature, it should be noted that here too the hinge center lies outside the prosthesis.

DETAILED DESCRIPTION OF THE INVENTION

Figure 1:
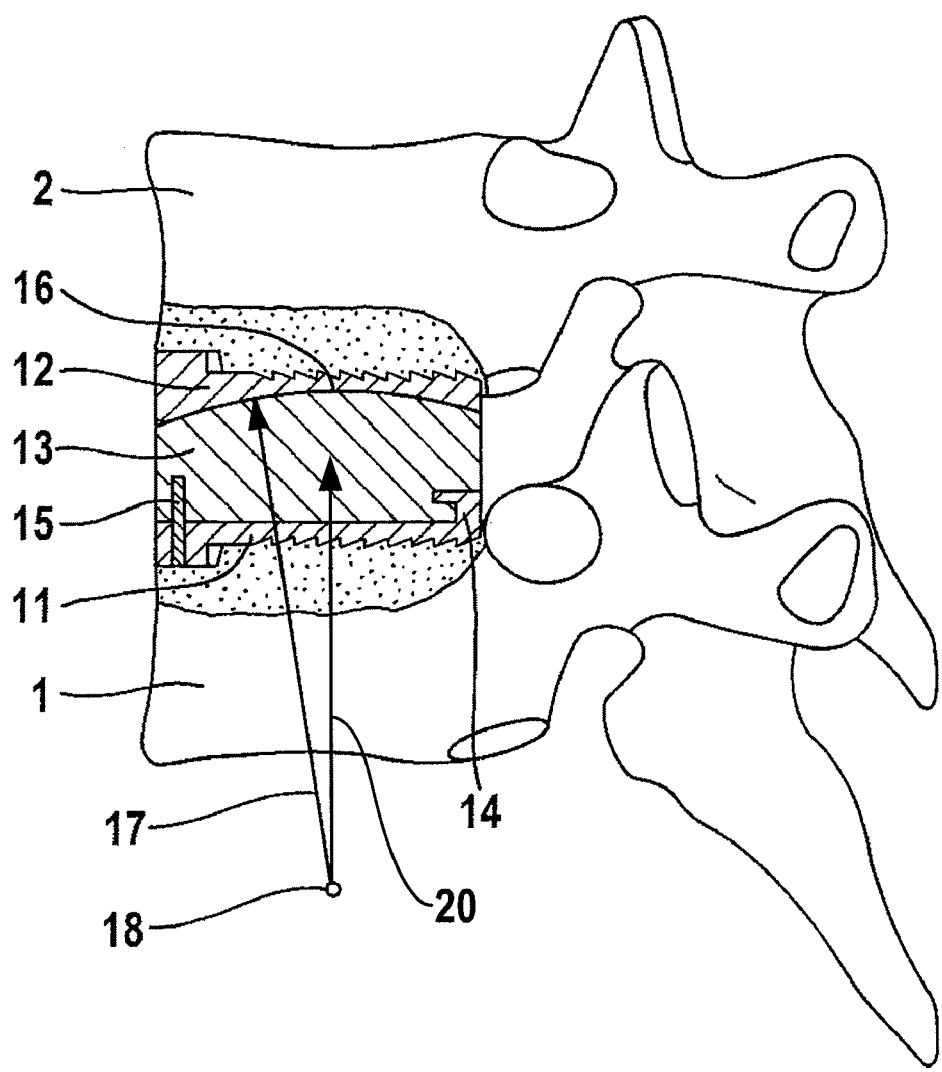
FIG. 1, depicts an illustrative embodiment to explain the terms used above.

An intervertebral prosthesis made up of a lower cover plate 11, an upper cover plate 12 and a prosthetic core 13 is fitted between the vertebral bodies 1 and 2. The prosthetic core 13 is held securely on the lower cover plate 11 by an undercut ledge 14, running along three sides of the prosthesis, and by a catch 15. With the upper cover plate 12, it forms a spherical slide surface pair 16 having a slide surface radius 17 and a center of curvature 18 which forms the center of movement of the hinge formed by the prosthesis. This means that the cover plates 11, 12 and the vertebrae 1, 2 connected to them are able to execute a relative movement with respect to one another which represents a rotation movement about the center 18 as long as the slide surface pair 16 alone determines the relative movement. In practice, other slide surfaces, namely the articular facets, are also involved in determining the relative movement, so that the relative movement actually taking place may deviate a little from this. It will however be appreciated that the hinge movement is all the more harmonious, and continuation of the patient's symptoms all the more unlikely, the more the center 18 of the hinge movement defined by the prosthesis agrees with the natural center of movement. The hinge radius 20 is defined independently of the slide surface radius and differs from the latter in that it is measured from the center 18 of the hinge movement to the geometric midpoint of the prosthesis.

The prostheses intended for the more cranial intervertebral spaces (in particular C2/C3 and C3/C4) are distinguished on the one hand by a larger hinge radius than in the prostheses which are intended for the more caudal intervertebral spaces (in particular C5/C6 and C6/C7). On the other hand, the prostheses to be fitted more in the cranial direction can have a smaller surface extent in particular in the AP direction (AP=anteroposterior) than the prostheses to be fitted more in the caudal direction can. Thus, a further characteristic feature of the invention lies in the fact that the set of intervertebral prostheses comprises at least one first prosthesis whose hinge radius is greater and whose surface extent (in particular in the AP direction) is smaller than those of a second prosthesis.

The invention claimed is:

1. A method for implanting prostheses by determining which cervical intervertebral prostheses of a cervical intervertebral prosthesis system comprising a plurality of intervertebral prostheses of different hinge radii are suitable for replacing cervical intervertebral disks, comprising:
    providing a cervical intervertebral prosthesis system comprising at least first and second different prostheses for replacement of at least first and second intervertebral disks, each of which has a hinge with a predefined center of hinge movement, wherein the different prostheses have different positions of the center of hinge movement,
    determining the hinge radii of first and second affected joints, the first affected joint being associated with the first intervertebral disk and the second affected joint being associated with a second intervertebral disk,
    selecting the first prosthesis with a hinge radius approximating the hinge radius of the first affected joint to replace the first intervertebral disk,
    selecting the second prosthesis with a hinge radius approximating the hinge radius of the second affected joint to replace the second intervertebral disk, the first intervertebral disk lying in a cranial direction relative to the second intervertebral disk, and
    implanting the selected prostheses into the affected joints, wherein
    the first prosthesis has a smaller extent in an anterior-posterior direction and slide surface with a greater radius of curvature than the extent in the anterior-posterior direction and radius of curvature of the slide surface of the second prosthesis.

2. The method according to claim 1, wherein at least one prosthesis has a slide surface radius above 18 mm and at least one prosthesis has a slide surface radius below 18 mm.

3. The method according to claim 2, wherein at least one prosthesis has a slide surface radius below 15 mm.

4. A method for implanting a prosthesis by determining which cervical intervertebral prostheses of a cervical intervertebral prosthesis system comprising at least first and second different prostheses for replacement of at least first and second intervertebral disks, each of which has a hinge with a predefined center of hinge movement and comprises a pair of slide surfaces configured to form the hinge, and wherein the different prostheses have different positions of the center of hinge movement and have slide surfaces with different radii of curvature, are suitable for replacing at least two cervical intervertebral disks, the method comprising:
    providing the cervical intervertebral prosthesis system,
    determining the hinge radii of at least first and second affected joints, the first affected joint being associated with the first intervertebral disk and the second affected joint being associated with the second intervertebral disk,
    selecting the first one of the different prostheses of the system to replace the first intervertebral disk,
    selecting the second one of the different prostheses to replace the second intervertebral disk, the first intervertebral disk lying in a cranial direction relative to the second intervertebral disk, and
    implanting the selected prostheses into the affected joints,
    so that the first one of the different prostheses has slide surfaces with a greater radius of curvature than the radius of curvature of the slide surfaces of the second one of the different prostheses of the system which is selected to replace the second intervertebral disk.

* * * * *